(12) United States Patent
Iida et al.

(10) Patent No.: US 11,497,903 B2
(45) Date of Patent: Nov. 15, 2022

(54) CONNECTION DEVICE AND CONNECTION DEVICE SET

(71) Applicant: OLYMPUS CORPORATION, Tokyo (JP)

(72) Inventors: Tadafumi Iida, Hachioji (JP); Kyota Sawai, Fussa (JP)

(73) Assignee: OLYMPUS CORPORATION, Tokyo (JP)

( * ) Notice: Subject to any disclaimer, the term of this patent is extended or adjusted under 35 U.S.C. 154(b) by 308 days.

(21) Appl. No.: 16/718,744

(22) Filed: Dec. 18, 2019

(65) Prior Publication Data

US 2020/0121906 A1 Apr. 23, 2020

Related U.S. Application Data

(63) Continuation of application No. PCT/JP2018/016837, filed on Apr. 25, 2018.

(30) Foreign Application Priority Data

Jul. 5, 2017 (JP) .............................. JP2017-132129

(51) Int. Cl.
*A61M 25/16* (2006.01)
*A61M 25/18* (2006.01)
(Continued)

(52) U.S. Cl.
CPC .............. *A61M 39/10* (2013.01); *A61M 5/31* (2013.01)

(58) Field of Classification Search
CPC ......... A61M 39/10; A61M 39/12; F16L 33/24
See application file for complete search history.

(56) References Cited

U.S. PATENT DOCUMENTS 5,399,173 A * 3/1995 Parks .................. A61J 15/0026
16/2.1
5,489,274 A 2/1996 Chu et al.
(Continued)

FOREIGN PATENT DOCUMENTS

EP  1 148 281 A1  10/2001
EP  1 894 597 A1   3/2008
(Continued)

OTHER PUBLICATIONS

International Search Report dated Jul. 24, 2018 received in PCT/JP2018/016837.

*Primary Examiner* — Rebecca E Eisenberg
(74) *Attorney, Agent, or Firm* — Scully, Scott, Murphy & Presser, P.C.

(57) ABSTRACT

A connection device includes a tube that is branched to two passages from a branch portion and includes a first and second branch tubes provided on one end side as a liquid-feeding destination, a first protruding plate that includes, on another end side, first another end edge provided in a direction orthogonal to an axis line of the first branch tube and that is provided so as to protrude from an outer circumference portion of the tube, and a second protruding plate that is provided so as to face the first protruding plate across the tube and protrude in a diameter direction of the tube and that includes, on the other end side, second another end edge provided so as to be orthogonal to an axis line of the second branch tube.

9 Claims, 15 Drawing Sheets

(51) Int. Cl.
*A61M 39/00* (2006.01)
*A61M 39/10* (2006.01)
*A61M 5/31* (2006.01)

(56) References Cited

U.S. PATENT DOCUMENTS

| | | | |
|---|---|---|---|
| 6,689,096 B1 * | 2/2004 | Loubens | A61M 29/02 |
| | | | 600/7 |
| 2008/0054632 A1 | 3/2008 | Funamura et al. | |
| 2011/0060286 A1 | 3/2011 | Tanabe et al. | |
| 2016/0339226 A1 * | 11/2016 | Sealfon | A61M 39/12 |
| 2017/0119997 A1 * | 5/2017 | Burkholz | A61M 25/0043 |

FOREIGN PATENT DOCUMENTS

| | | |
|---|---|---|
| EP | 2 260 894 A1 | 12/2010 |
| JP | 60-501042 A | 7/1985 |
| JP | 03-053317 U | 5/1991 |
| JP | 07-500981 A | 2/1995 |
| JP | 2001-061773 A | 3/2001 |
| JP | 2003-517324 A | 5/2003 |
| JP | 3116021 U | 11/2005 |
| JP | 2008-054927 A | 3/2008 |
| JP | 2012-219942 A | 11/2012 |
| WO | 84/04043 A1 | 10/1984 |
| WO | 93/06877 A1 | 4/1993 |
| WO | 2009/123024 A1 | 10/2009 |

* cited by examiner

US 11,497,903 B2

CONNECTION DEVICE AND CONNECTION DEVICE SET

CROSS REFERENCE TO RELATED APPLICATION

This application is a continuation application of PCT/JP2018/016837 filed on Apr. 25, 2018 and claims benefit of Japanese Application No. 2017-132129 filed in Japan on Jul. 5, 2017, the entire contents of which are incorporated herein by this reference.

BACKGROUND OF THE INVENTION

1. Field of the Invention

The present invention relates to a connection device and a connection device set.

2. Description of the Related Art

Conventionally, a connection device that connects a liquid-feeding device and a liquid-feeding destination has been used so as to feed a liquid to the liquid-feeding destination such as a tube by the liquid-feeding device such as a syringe. In Japanese Patent Application Laid-Open Publication No. 2001-61773, for example, a connection device one end of which is connected to a syringe and the other end of which is connected to a tube connected to an endoscope to thereby connect the syringe and the tube is disclosed. The connection device has a pair of grasping rings that protrude from an outer wall surface of a connector body to right and left and can be grasped by fingers.

SUMMARY OF THE INVENTION

A connection device according to one aspect of the present invention includes a tube that is branched to two passages from a branch portion and includes a first and second branch tubes provided on one end side as a liquid-feeding destination, a first protruding plate that includes, on another end side, first another end edge provided in a direction orthogonal to an axis line of the first branch tube and that is provided so as to protrude from an outer circumference portion of the tube, and a second protruding plate that is provided so as to face the first protruding plate across the tube and protrude in a diameter direction of the tube and that includes, on the other end side, second another end edge provided so as to be orthogonal to an axis line of the second branch tube.

A connection device set according to one aspect of the present invention includes a connection device including a tube that is branched to two passages from a branch portion and includes a first and second branch tubes provided on one end side as a liquid-feeding destination, a first protruding plate that includes, on another end side, first another end edge provided in a direction orthogonal to an axis line of the first branch tube and that is provided so as to protrude from an outer circumference portion of the tube, a second protruding plate that is provided so as to face the first protruding plate across the tube and protrude in a diameter direction of the tube and that includes, on the other end side, second another end edge provided so as to be orthogonal to an axis line of the second branch tube, and a jig that is abutted to the first and second other end edges when a flexible tube is connected to the tube.

DETAILED DESCRIPTION OF THE PREFERRED EMBODIMENT(S)

Figure 1:
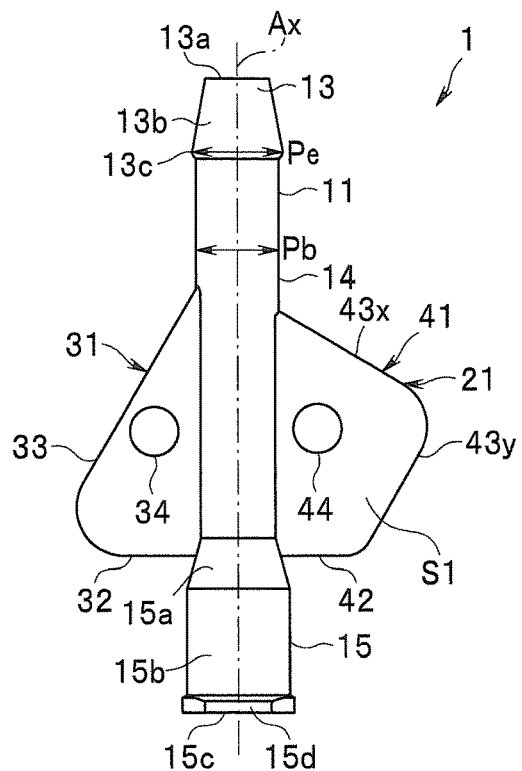
FIG. 1 is a front view of a connection device according to an embodiment of the present invention.
Figure 2:
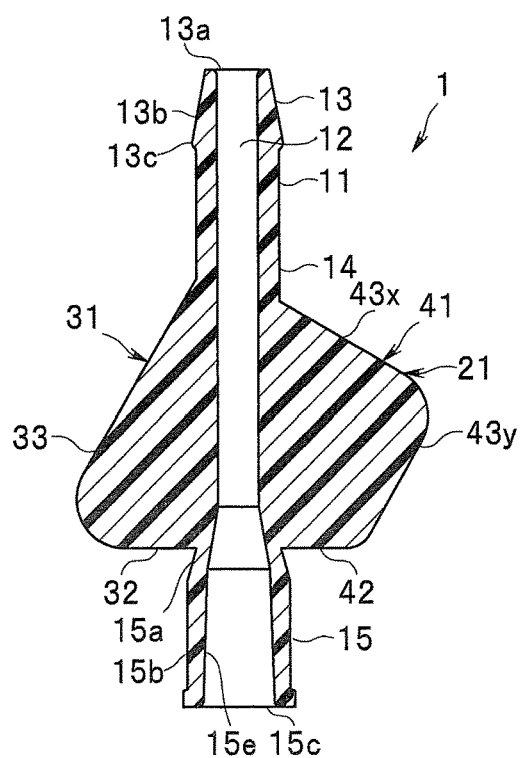
FIG. 2 is a cross-section view in an axial direction of the connection device according to the embodiment of the present invention.
Figure 3:
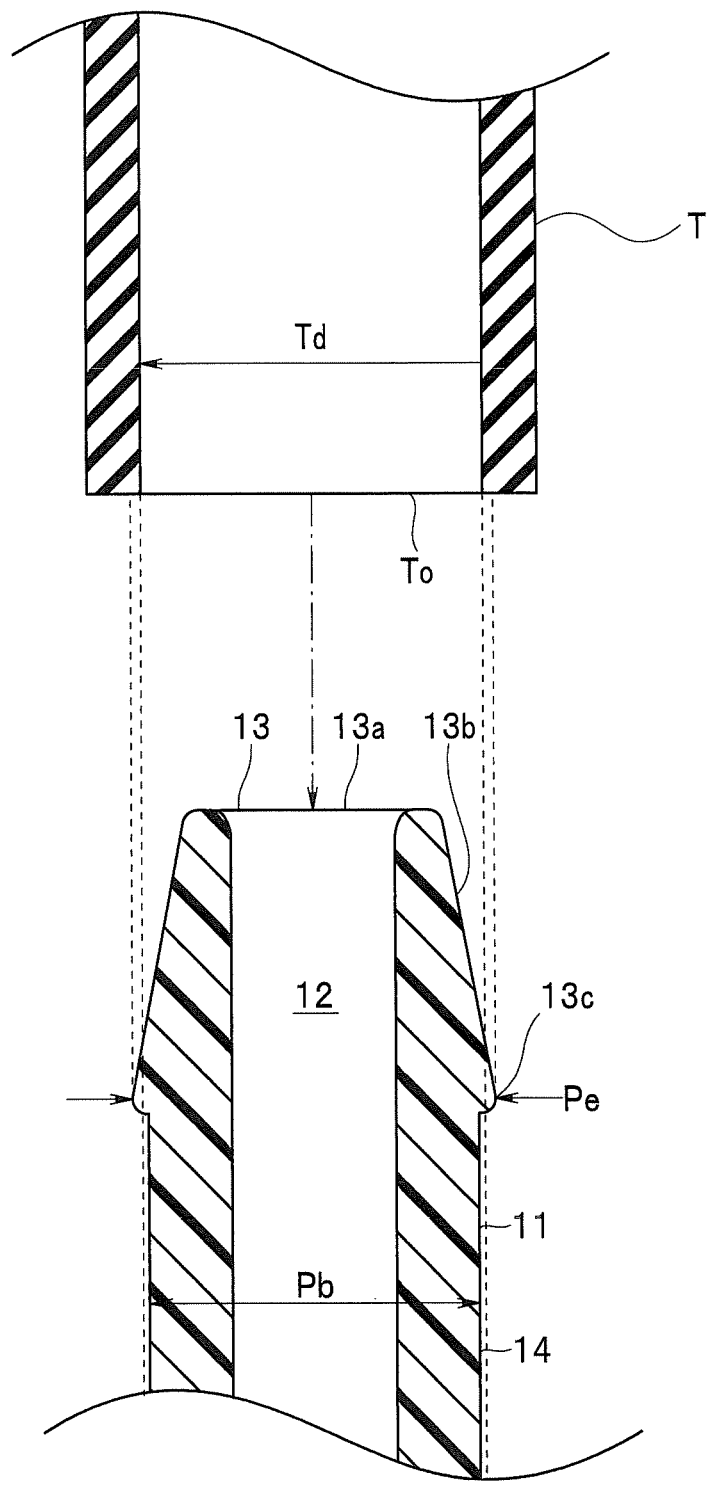
FIG. 3 is an explanatory diagram for explaining a body portion outer diameter and an enlarged diameter portion outer diameter of the connection device according to the embodiment of the present invention.
Figure 4:
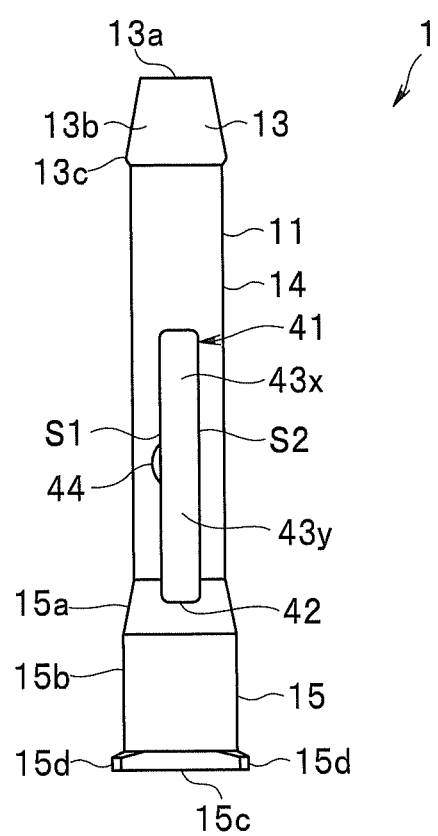
FIG. 4 is a side view of the connection device according to the embodiment of the present invention.
Figure 5:
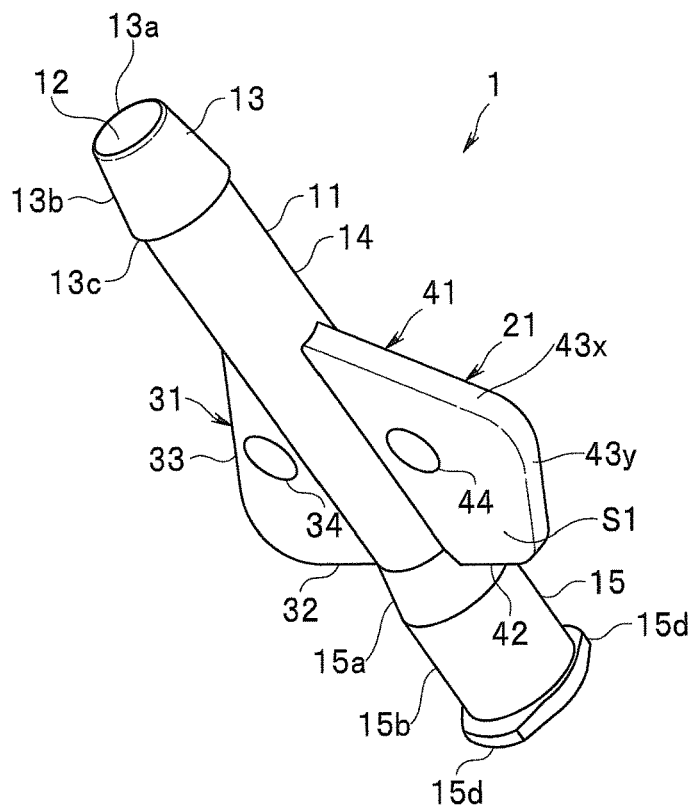
FIG. 5 is a perspective view of the connection device according to the embodiment of the present invention.
Figure 6:
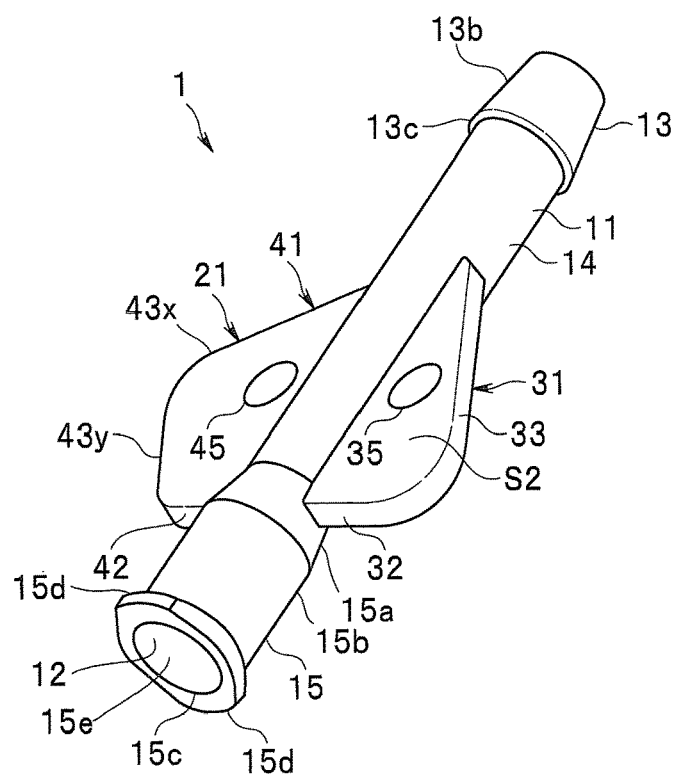
FIG. 6 is a perspective view of the connection device according to the embodiment of the present invention.
Figure 7:
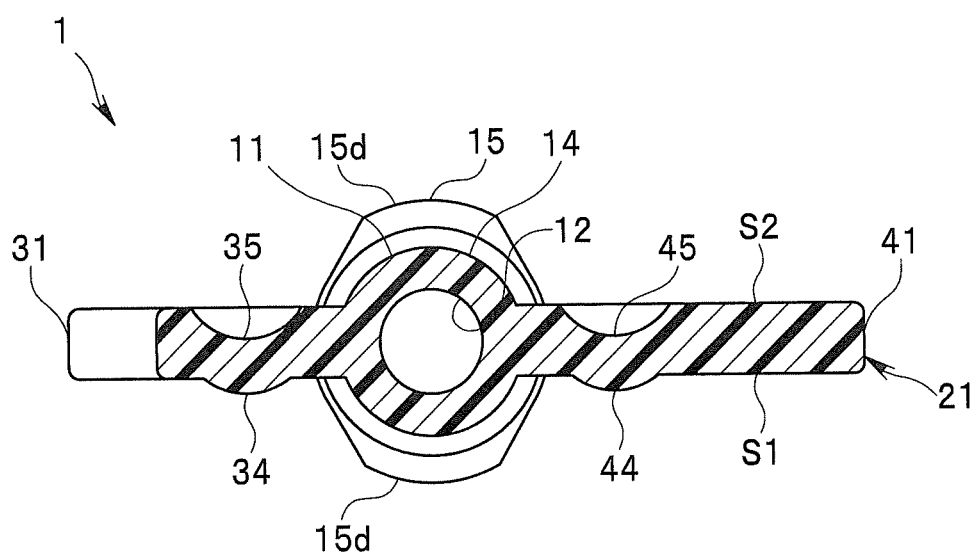
FIG. 7 is a cross-section view in a direction orthogonal to an axis line of the connection device according to the embodiment of the present invention.

Hereinafter, an embodiment of the present invention will be described with reference to drawings.
(Configuration of Connection Device)
FIGS. 1 to 7 are diagrams of a connection device 1 according to the embodiment of the present invention. FIG. 1 is a front view, FIG. 2 is a cross-section view in a direction of an axis line Ax, FIG. 3 is an explanatory diagram for explaining a body portion outer diameter Pb and an enlarged diameter portion outer diameter Pe, FIG. 4 is a side view, FIGS. 5 and 6 are perspective views, and FIG. 7 is a cross-section view in a direction orthogonal to the axis line Ax.

As shown in FIGS. 1 to 7, the connection device 1 is, for example, made of a material of resins. The connection device 1 has a tube 11 and a protruding portion 21.

The tube 11 is formed in a cylindrical shape and has a flow path 12 for flowing a fluid inside (FIG. 2). The tube 11 has a tube connection portion 13 provided in one end portion, a body portion 14 provided in a central portion, and a luer lock 15 provided in the other end portion.

The tube connection portion 13 has a one end opening 13a that is provided at one end and communicates with the flow path 12, a taper portion 13b that has a diameter enlarging from an outer edge of the one end opening 13a in the other end direction, and an enlarged diameter portion 13c that is provided on the other end side of the taper portion 13b and has the enlarged diameter portion outer diameter Pe.

A flexible tube T connected to the tube connection portion 13 is made of a material of an elastically deformable resin such as rubber (FIG. 3). The flexible tube T has a tube inner diameter Td. An outer edge of the one end opening 13a is set to be smaller than the tube inner diameter Td. The enlarged diameter portion outer diameter Pe is set to be larger than the tube inner diameter Td.

The body portion 14 has the body portion outer diameter Pb and extends from the tube connection portion 13 in the other end direction. The body portion outer diameter Pb is set to be equal to or smaller than the enlarged diameter portion outer diameter Pe and the tube inner diameter Td.

In other words, a relationship among the body portion outer diameter Pb, the tube inner diameter Td, and the enlarged diameter portion outer diameter Pe is set to Pb≤Td<Pe. In other words, the body portion outer diameter Pb of the tube 11 is set to be equal to or smaller than the tube inner diameter Td of the flexible tube T. Further, the enlarged diameter portion outer-diameter Pe of the enlarged diameter portion 13c provided in one end portion is set to be larger than the tube inner diameter Td.

The luer lock 15 is formed in a female luer shape. The luer lock 15 has a conical plane portion 15a that extends from the body portion 14 in the other end direction and is formed in a conical surface shape so as to extend a diameter, a short cylinder portion 15b that extends from the conical plane portion 15a in the other end direction and is formed in a short cylinder shape, the other end opening 15c that is provided in the other end and communicates with the flow path 12, a pair of screw protrusions 15d that are provided at an outer edge of the other end opening 15c and protrude from an outer circumferential portion, and a luer taper 15e in which a diameter of an inner circumference surface of the tube 11 enlarges from one end side of the luer lock 15 to the other end opening 15c (FIG. 2). In other words, the luer lock 15 to which a syringe is connectable is arranged at the other end portion of the tube 11.

The protruding portion 21 has protruding plates 31 and 41. Each of the protruding plates 31 and 41 has a predetermined thickness smaller than a diameter of the tube 11, protrudes from the outer circumference portion of the tube 11 in a diameter direction of the tube 11 on the other end side of the tube 11, and is formed in a flat plate shape extending along a flat surface including the axis line Ax of the tube 11. Further, each of the protruding plates 31 and 41 is provided so as to face each other across the axis line Ax of the tube 11 and protrude from the tube 11 in the diameter direction of the tube 11 and in the opposite direction to each other.

A protruding plate 31 that is a first protruding plate has an other end edge 32 that is a first other end edge, a side edge 33 that is a first side edge, a convex portion 34 that is a first convex portion, and a concave portion 35 that is a first concave portion.

The other end edge 32 is provided so as to protrude from the tube 11 in the diameter direction of the tube 11 on the other end side of the protruding plate 31.

The side edge 33 extends in a direction inclined in such a manner that a distance from the tube 11 is shortened toward one end from the end portion of the other end edge 32 on the side portion side of the protruding plate 31, and intersects the tube 11. An intersection site between the other end edge 32 and the side edge 33 is formed so as to be bent in an arc.

In other words, the protruding plate 31 is formed in a substantially triangle by the body portion 14, the other end edge 32, and the side edge 33 in an outer circumference shape.

As shown in FIG. 7, the convex portion 34 is provided on one surface side S1 of front and rear faces of the protruding plate 31 and is formed in a semi-spherical convex shape.

The concave portion 35 is provided on the other surface side S2 of the front and rear faces of the protruding plate 31, which is a side opposite to the convex portion 34 across the protruding plate 31 and is formed in a semi-spherical concave shape.

Returning to FIGS. 1 to 6, a protruding plate 41 that is a second protruding plate has an other end edge 42 that is a second other end edge, a side edge 43 that is a second side edge, a convex portion 44 that is a second convex portion, and a concave portion 45 that is a second concave portion.

The other end edge 42 is provided so as to protrude from the tube 11 in the diameter direction of the tube 11 on the side opposite to the other end edge 32 across the tube 11 and on the other end side of the protruding plate 41.

The other end edges 32 and 42 are arranged on the same flat surface orthogonal to the axis line Ax. In other words, the other end edges 32 and 42 are formed so as to be orthogonal to the axis line Ax.

In the side portion side of the protruding plate 41, the side edge 43 has an other end side edge 43y that extends in the direction inclined in such a manner that a distance from the tube 11 is lengthened toward one end from an end portion of the other end edge 42 and a one end side edge 43x that extends in the direction inclined in such a manner that a distance from the tube 11 is shortened toward one end from an end portion of the other end side edge 43y, and intersects the tube 11. An intersection site between the other end edge 42 and the other end side edge 43y and an intersection site between the other end side edge 43y and the one end side edge 43x are formed so as to be bent in an arc. It does not matter if the other end side edge 43y is formed to be parallel to the side edge 33.

In other words, in the outer circumference shape, the protruding plate 41 is formed in a substantially quadrangle by the tube 11, the other end edge 42, the other end side edge 43y, and one end side edge 43x. The protruding plate 41 is formed to be larger than the protruding plate 31 in a surface area.

As shown in FIG. 7, the convex portion 44 is provided on the one surface side S1 of front and rear faces of the protruding plate 41 and is formed in a semi-spherical convex shape.

The concave portion 35 is provided on the other surface side S2 of the front and rear faces of the protruding plate 41, which is a side opposite to the one surface side S1 of the protruding plate 41 and is formed in a semi-spherical concave shape.

Each of the convex portion 34, the concave portion 35, the convex portion 44, and the concave portion 45 is provided on the same flat surface orthogonal to the axis line Ax of the tube 11.

(Configuration of Jig J)

A configuration of a jig J that fixes the connection device 1 will be described.

Figure 8:
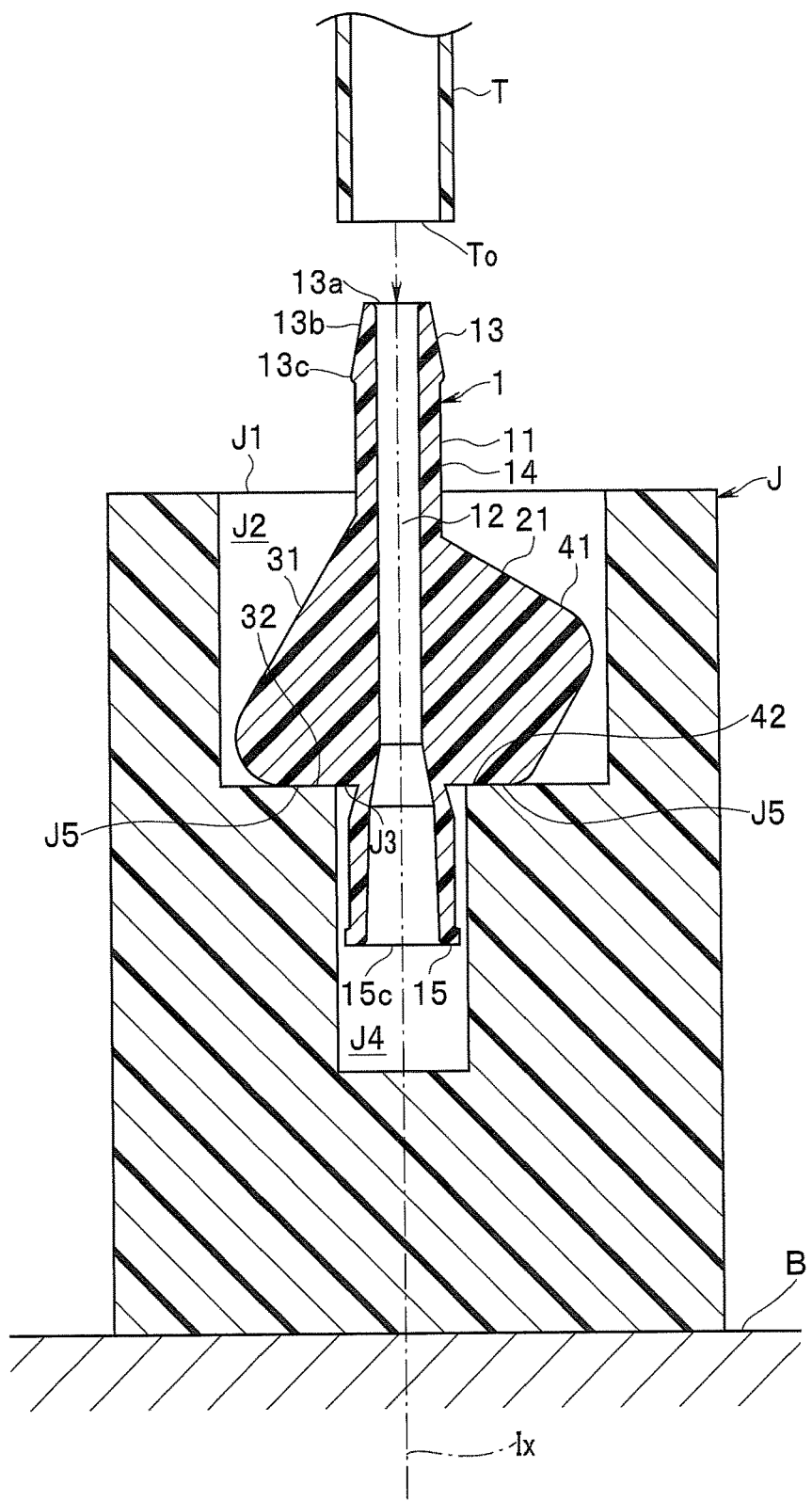
FIG. 8 is an explanatory diagram for explaining an example of connection work between the connection device using a jig and a flexible tube according to the embodiment of the present invention.

FIG. 8 is an explanatory diagram for explaining an example of connection work between the connection device 1 using the jig J and the flexible tube T according to the embodiment of the present invention.

As shown in FIG. 8, the jig J is made of a material of resins, metal, or the like and is formed in a block shape such as a rectangular column. For example, the jig J can be mounted on a mounting place B of a desk, a platform, a floor, or the like. The jig J has an opening J1, a protruding portion housing portion J2, an opening for tube J3, a tube housing portion J4, and a stopper portion J5.

The opening J1 is provided on a top surface of the jig J. For example, the opening J1 is formed in a quadrangular shape having a predetermined vertical width and horizontal width. The connection device 1 can be inserted into a jig having the predetermined vertical width and horizontal width. The vertical width and the horizontal width are adjusted and set so that the inserted connection device 1 does not fall down within the jig J.

The protruding portion housing portion J2 is concaved from the opening J1. A peripheral wall of the protruding portion housing portion J2 extends from the opening J1. A length in a depth direction of the protruding portion housing portion J2 is set to a length in which the tube connection portion 13 protrudes from the upper surface. The length in the depth direction of the protruding portion housing portion J2 is desirably longer than a length in a direction of the axis line Ax of the protruding portion 21 so that the connection device 1 is stabilized. However, it does not matter if the length in the depth direction of the protruding portion housing portion J2 is set to be shorter than the length in the direction of the axis line Ax of the protruding portion 21.

The opening for tube J3 is provided in the center of a bottom portion of the protruding portion housing portion J2. The opening for tube J3 has an inner diameter larger than an outer diameter of the tube 11 so as to insert the tube 11.

The tube housing portion J4 is concaved from the opening for tube J3. A length in a depth direction of the tube housing portion J4 is set to be longer than a length from the other end edges 32 and 42 to the other end of the tube 11 so that the other end of the tube 11 does not hit against a bottom surface of the tube housing portion J4.

The stopper portion J5 is provided on both sides across the opening for tube J3 in the bottom portion of the protruding portion housing portion J2. The stopper portion J5 is provided on a flat surface orthogonal to an insertion axis line Ix.

(Action)

The connection work between the connection device 1 using the jig J and the flexible tube T will be described.

A user directs the opening J1 upward and places the jig J on the mounting place B.

The user attaches the connection device 1 to the jig J. Specifically, the user inserts the connection device 1 into the jig J from the other end portion along the insertion axis line Ix. When the connection device 1 is inserted into the jig J, the other end portion of the tube 11 is internally inserted into the tube housing portion J4 through the opening J1, the protruding portion housing portion J2, and the opening for tube J3. When the connection device 1 is further inserted into the jig J, the other end edges 32 and 42 are abutted to the stopper portion J5.

The user grasps the flexible tube T and externally fits and pushes an end portion opening To of the flexible tube T to an outer edge of one end opening 13*a* of the tube connection portion 13. The other end edges 32 and 42 are stopped by the stopper portion J5 and an end portion of the flexible tube T has a diameter enlarging along the taper portion 13*b* by an elastic deformation and is externally inserted into the taper portion 13*b*. When the end portion opening To of the flexible tube T is further pushed, passes through the enlarged diameter portion 13*c*, and reaches the body portion 14, a diameter of the end portion of the flexible tube T shortens by a restoring force.

In other words, the flexible tube T is connected to one end portion of the tube 11. The protruding portion 21 is provided on the other end side of the tube 11, protrudes from the outer circumference portion of the tube 11 in the diameter direction of the tube 11, and is formed in a flat plate shape widened along a flat surface including the axis line Ax of the tube 11. Further, when the flexible tube T is connected to the tube 11, the other end edge 32 formed on the other end side is abutted to the jig J.

Thereby, a press force is received by the stopper portion J5 through the other end edges 32 and 42 without dispersion of the press force. Accordingly, at the time of the connection work, the connection device 1 is stably retained by the jig J.

According to the above-described embodiment, the connection device 1 is attached to the jig J, and in a stable state, the flexible tube T can be connected to the connection device 1 and a work efficiency of the connection work can be caused to be improved.

(Modification 1 of Embodiment)

In the embodiment, the other end edges 32 and 42 are arranged on the same flat surface orthogonal to the axis line Ax. However, it does not matter if the other end edges 32 and 42 are not arranged on the same flat surface orthogonal to the axis line Ax.

Figure 9:
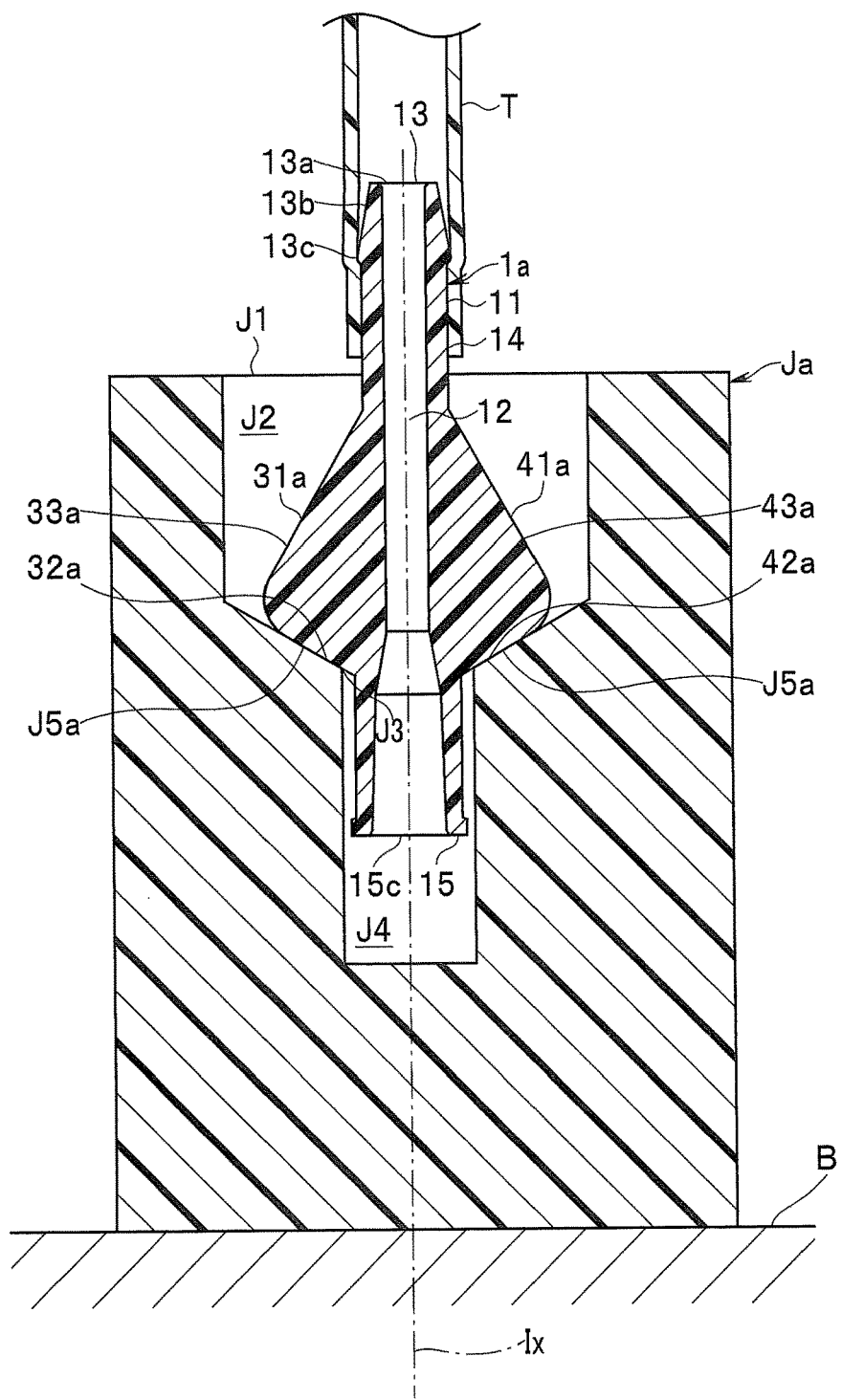
FIG. 9 is a cross-section view in an axial direction of the connection device according to a modification 1 of the embodiment of the present invention.

FIG. 9 is a cross-section view in the direction of the axis line Ax of a connection device 1*a* according to a modification 1 of the embodiment of the present invention. In the modification, regarding configurations similar to the configurations of the other embodiments and modifications, descriptions are omitted.

The connection device 1*a* has protruding plates 31*a* and 41*a*.

The protruding plate 31*a* has an other end edge 32*a* and a side edge 33*a*.

In the other end side of the protruding plate 31*a*, the other end edge 32*a* protrudes from the tube 11 and extends in the direction inclined in such a manner that a distance from the tube 11 is lengthened toward one end.

The side edge 33*a* extends in a direction inclined in such a manner that a distance from the tube 11 is shortened toward one end from an end portion of the other end edge 32*a* on the side portion side of the protruding plate 31*a*, and intersects the tube 11.

A protruding plate 41*a* has an other end edge 42*a* and a side edge 43*a*.

The other end edge 42*a* protrudes from the tube 11 and extends in a direction inclined in such a manner that a distance from the tube 11 is lengthened toward one end, on the opposite side to the other end edge 32*a* across the tube 11 and on the other end side of the protruding plate 41a. In other words, the other end edges 32a and 42a are formed to intersect the axis line Ax.

The side edge 43a extends in a direction inclined in such a manner that a distance from the tube 11 is shortened toward one end from an end portion of the other end edge 42a on a side portion side of the protruding plate 41a, and intersects the tube 11.

A jig Ja has a stopper portion J5a.

The stopper portion J5a is provided in an inclination direction similar to the inclination directions of the other end edges 32a and 42a so as to face the other end edges 32a and 42a of the connection device 1a inserted along the insertion axis line Ix. Specifically, the stopper portion J5a is provided on both sides across the opening for tube J3 and is provided in a direction inclined in such a manner that a distance from the insertion axis line Ix is mutually shortened toward a depth direction.

When the connection device 1a is inserted into the jig Ja, the other end portion of the tube 11 is internally inserted into the tube housing portion J4 through the opening J1, the protruding portion housing portion J2, and the opening for tube J3. When the connection device 1a is inserted shifting from the opening for tube J3, the other end portion of the tube 11 is contacted with the stopper portion J5a and is guided to an insertion opening.

After the connection device 1a is attached to the jig Ja, the user externally fits and pushes the flexible tube T to the connection device 1a grasping the flexible tube T. The other end edges 32a and 42a are stopped by the stopper portion J5a and the flexible tube T is connected to the tube connection portion 13.

Thereby, the connection device 1a is attached to the jig Ja, and in a stable state, the flexible tube T can be connected to the connection device 1a and the work efficiency of the connection work can be caused to be improved.

(Modification 2 of Embodiment)

In the embodiment and the modification 1, the tube 11 is not branched. However, it does not matter if the tube 11 is configured to be branched to two passages.

Figure 10:
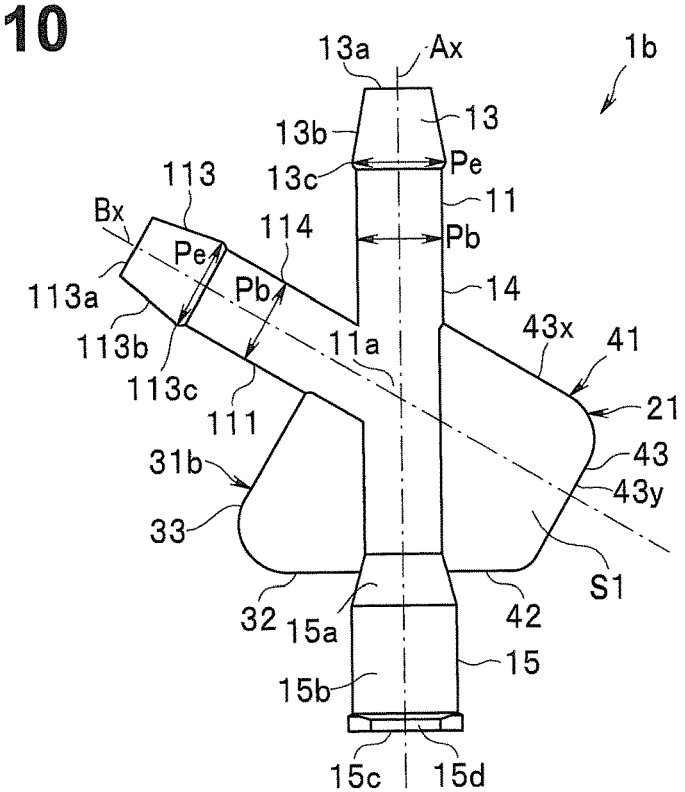
FIG. 10 is a front view of the connection device according to a modification 2 of the embodiment of the present invention.
Figure 11:
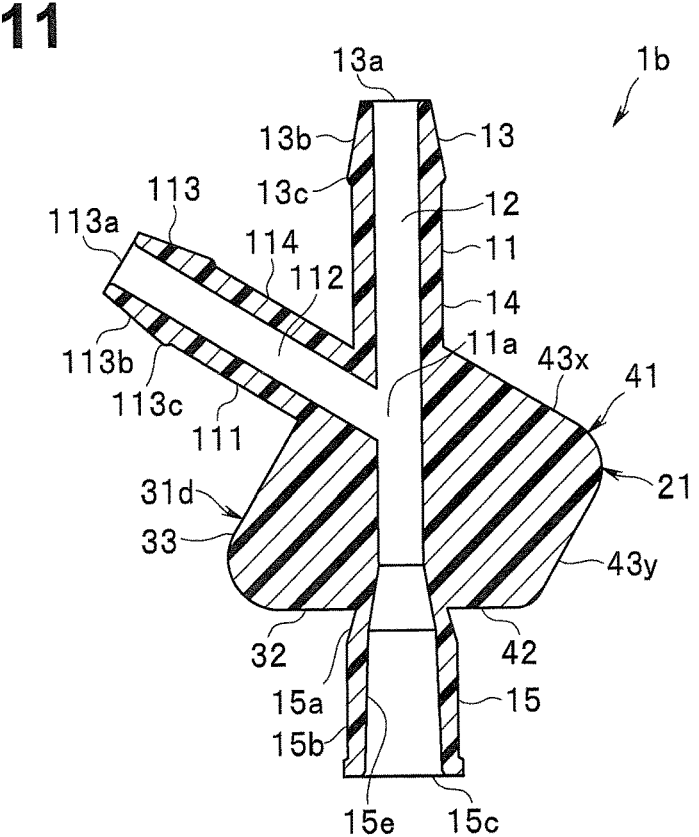
FIG. 11 is a cross-section view in an axial direction of the connection device according to the modification 2 of the embodiment of the present invention.

FIGS. 10 and 11 are diagrams for showing a connection device 1b according to a modification 2 of the embodiment of the present invention. FIG. 10 is a front view and FIG. 11 is a cross-section view in the direction of the axis line Ax. In the modification, regarding configurations similar to the configurations of the other embodiment and modifications, descriptions are omitted.

As shown in FIGS. 10 and 11, the connection device 1b has a branch portion 11a and a branch tube 111.

The branch portion 11a is provided in the tube 11.

In the branch portion 11a, the branch tube 111 is branched in a T shape from the tube 11 and extends in a direction inclined in such a manner that a distance from the tube 11 is lengthened toward the other end from the branch portion 11a. More specifically, the branch tube 111 extends in a direction opposite to the other end side edge 43y from the branch portion 11a along a direction orthogonal to the other end side edge 43y. The branch tube 111 is formed in a cylindrical shape and a flow path 112 for flowing a fluid is provided inside the branch tube 111. The branch tube 111 has a tube connection portion 113 and a body portion 114. Note that, as shown in FIG. 10, the other end side edge 43y is provided on both sides across an axis line Bx so as to be orthogonal to the axis line Bx of the branch tube 111.

The tube 11 is provided along a direction orthogonal to the other end edges 32 and 42. The tube 11 is branched to two passages on one end portion side.

The tube connection portion 113 has a branch end opening 113a that is provided at a branch end and communicates with a flow path 112 (FIG. 11), a taper portion 113b that has a diameter enlarging from an outer edge of the branch end opening 113a in a direction of the branch portion 11a, and an enlarged diameter portion 113c that is provided on the side of the branch portion 11a of the taper portion 113b and has the enlarged diameter portion outer diameter Pe.

The body portion 114 has the body portion outer diameter Pb and is provided to protrude from an outer circumference portion of the body portion 14 so as to be adjacent to a protruding plate 31b and so as to be orthogonal to the side edge 33.

A grasping portion 21 is formed by protruding plates 31b and 41 that protrude from the tube 11 to the diameter direction of the tube 11 across the branch portion 11a.

The protruding plate 31b is formed by the body portion 14, the other end edge 32, the side edge 33, and the body portion 114 in the outer circumference shape. Further, the protruding plate 31b is formed in an area of a substantially small quadrangle smaller than the area of the protruding plate 41.

Figure 12:
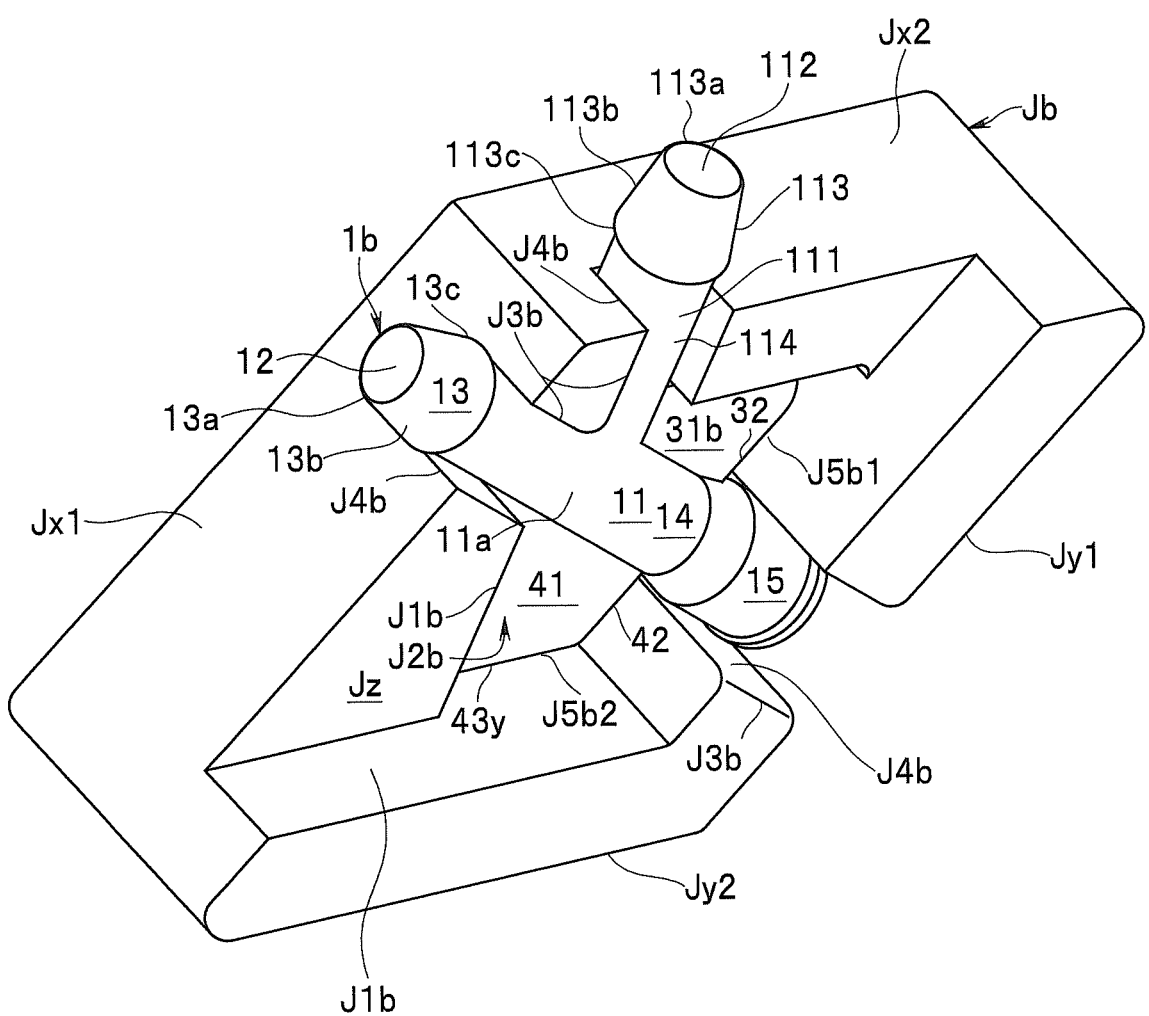
FIG. 12 is a perspective view of the connection device and the jig according to the modification 2 of the embodiment of the present invention.
Figure 13:
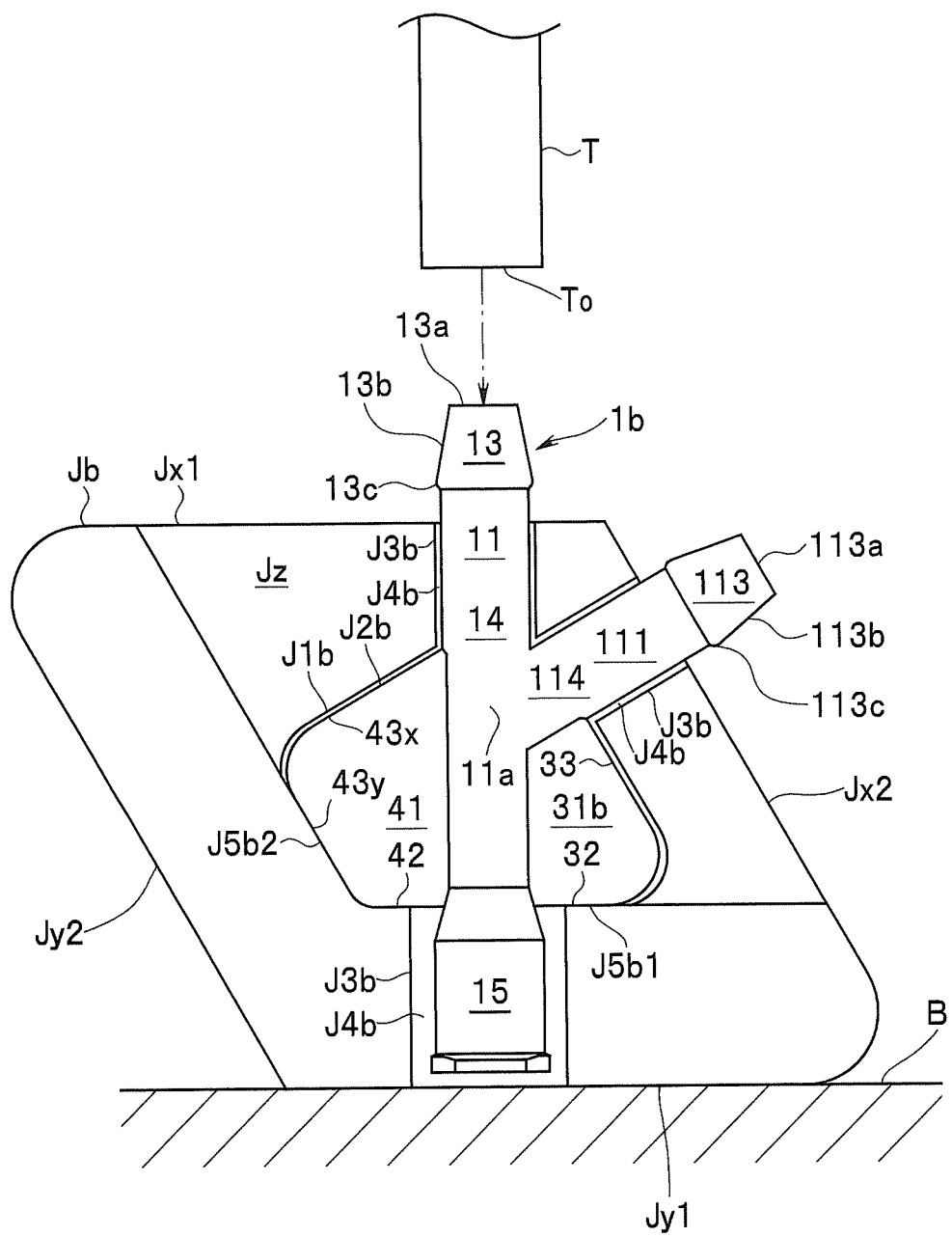
FIG. 13 is a front view of the connection device and the jig according to the modification 2 of the embodiment of the present invention.
Figure 14:
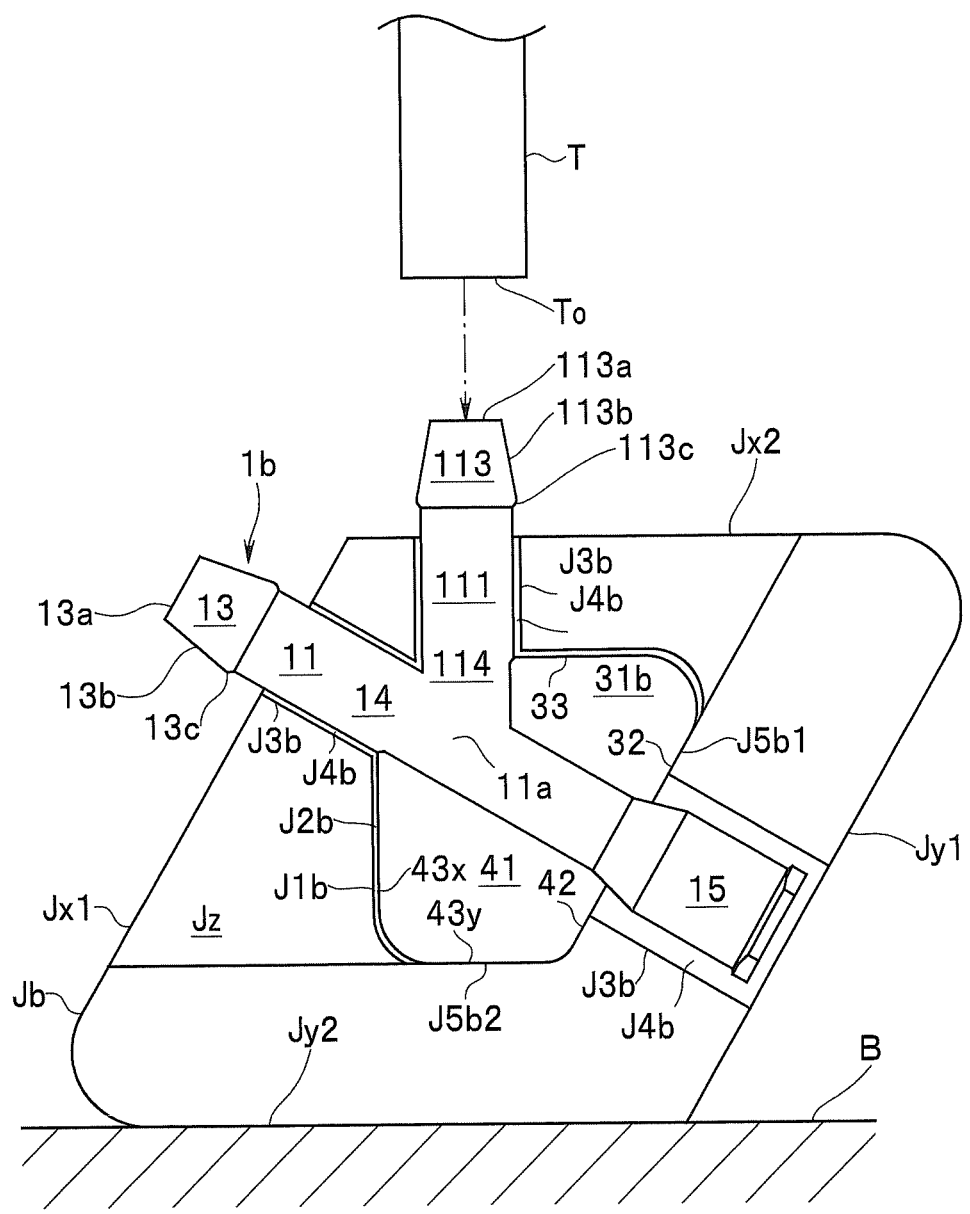
FIG. 14 is a front view of the connection device and the jig according to the modification 2 of the embodiment of the present invention.

FIGS. 12, 13, and 14 are diagrams showing the connection device 1b and a jig Jb according to the modification 2 of the embodiment of the present invention.

As shown in FIG. 12, the jig Jb is formed in a substantially rhombic column shape and has one end walls Jx1 and Jx2 and the other end walls Jy1 and Jy2 that surround four sides of the jig Jb. The one end wall Jx1 and the other end wall Jy1, and the one end wall Jx2 and the other end wall Jy2 are formed parallel to each other. A portion in which the one end wall Jx1 intersects the other end wall Jy2 and a portion in which the one end wall Jx2 intersects the other end wall Jy1 are formed so as to be bent in an arc.

Edge portions on the sides of the other end walls Jy1 and Jy2 of an end surface portion Jz are formed to protrude from the end surface portion Jz so that areas of the other end walls Jy1 and Jy2 are wider than the areas of the one end walls Jx1 and Jx2.

The jig Jb has an opening J1b, a protruding portion housing portion J2b, an opening for tube J3b, a tube housing portion J4b, and stopper portions J5b1 and J5b2.

The opening J1b is formed in the end surface portion Jz of the jig Jb along the outer circumference shape of the protruding plates 31b and 41 so that the other end edges 32 and 42 are parallel to the other end wall Jy1 and the other end side edge 43y is parallel to the other end wall Jy2.

The protruding portion housing portion J2b is concaved from the opening J1b. A circumferential wall of the protruding portion housing portion J2b extends from the opening J1b. A length in a depth direction of the protruding portion housing portion J2b is set to a length larger than the length of the body portion outer diameter Pb.

The opening for tube J3b is provided in the one end walls Jx1 and Jx2 and the other end wall Jy1 along shapes of the tube 11 and the branch tube 111.

The tube housing portion J4b is concaved from the opening for tube J3b. The tube housing portion J4b is formed in a shape of a through groove passing through each of the one end walls Jx1 and Jx2 and the other end wall Jy1 from the protruding portion housing portion J2b.

A stopper portion J5b1 is provided so as to be parallel to the other end wall Jy1 in an inner circumference of the protruding portion housing portion J2b.

A stopper portion J5b2 is provided so as to be parallel to the other end wall Jy2 in the inner circumference of the protruding portion housing portion J2b.

As shown in FIG. 13, the user attaches the connection device 1b to the jig Jb. More specifically, the user fits the protruding portion 21, and the tube 11 and the branch tube 111 in the opening J1b and the opening for tube J3b.

The user directs the other end wall Jy1 downward and places the jig Jb on the mounting place B so that the tube connection portion 13 is directed upward.

The user grasps the flexible tube T and externally fits and pushes the end portion opening To of the flexible tube T in an outer edge of the one end opening 13a of the tube connection portion 13. The other end edges 32 and 42 are stopped by the stopper portion J5b1 and the flexible tube T is connected to the tube connection portion 13.

As shown in FIG. 14, the user directs the other end wall Jy2 downward and places the jig Jb on the mounting place B so that the tube connection portion 113 is directed upward.

The user grasps the flexible tube T and externally fits and pushes the end portion opening To of the flexible tube T in an outer edge of the branch end opening 113a of the tube connection portion 113. The other end side edge 43y is stopped by the stopper portion J5b2 and the flexible tube T is connected to the tube connection portion 113.

Thereby, the connection device 1b is attached to the jig Jb, and in a stable state, the flexible tube T can be connected to each of the tube connection portions 13 and 113 and the work efficiency of the connection work can be caused to be improved.

(Modification 3 of Embodiment)

In the modification 2 of the embodiment, the tube 11 is branched in a T shape. However, it does not matter if the tube 11 is configured to be branched in a Y shape.

Figure 15:
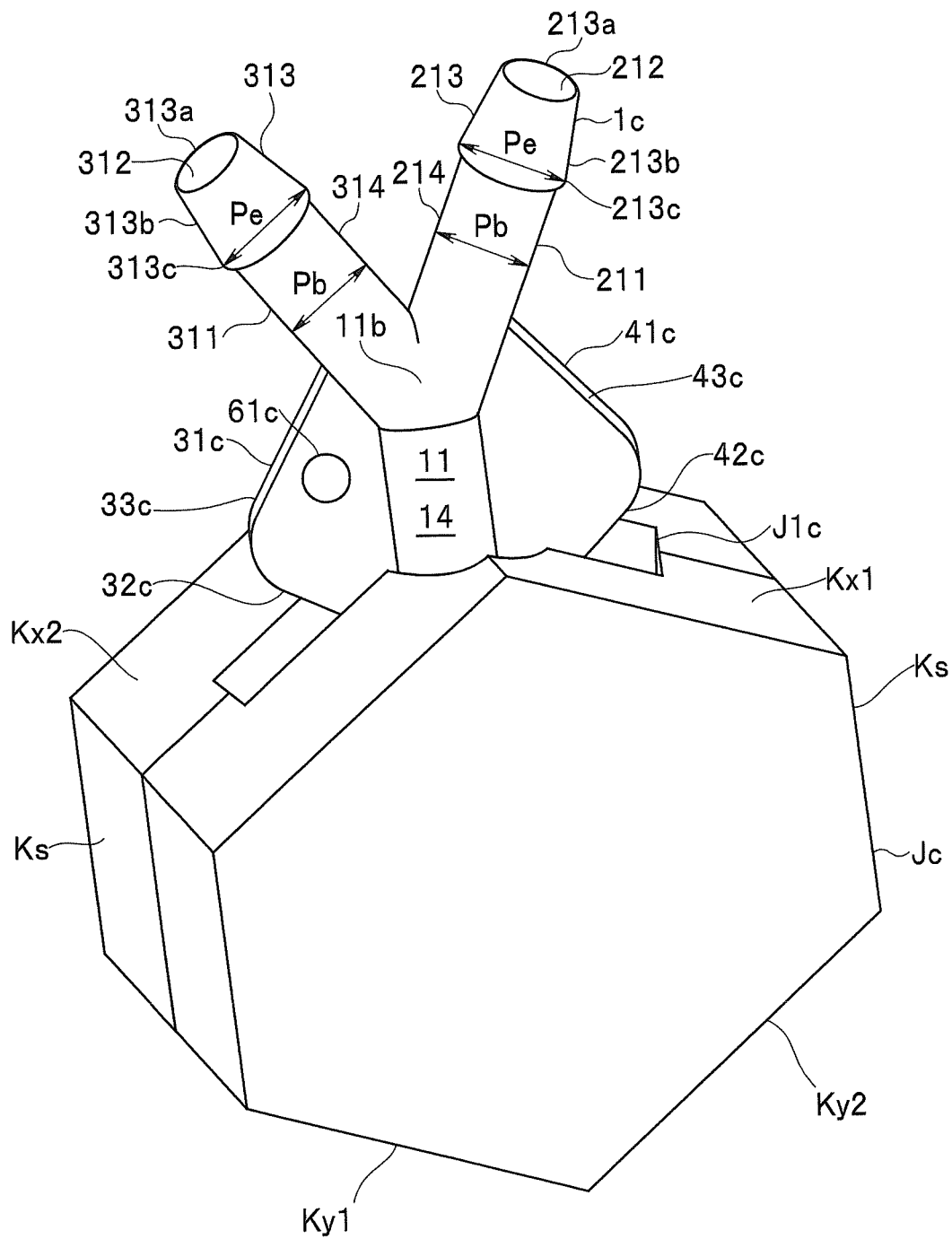
FIG. 15 is a perspective view of the connection device and the jig according to a modification 3 of the embodiment of the present invention.
Figure 16:
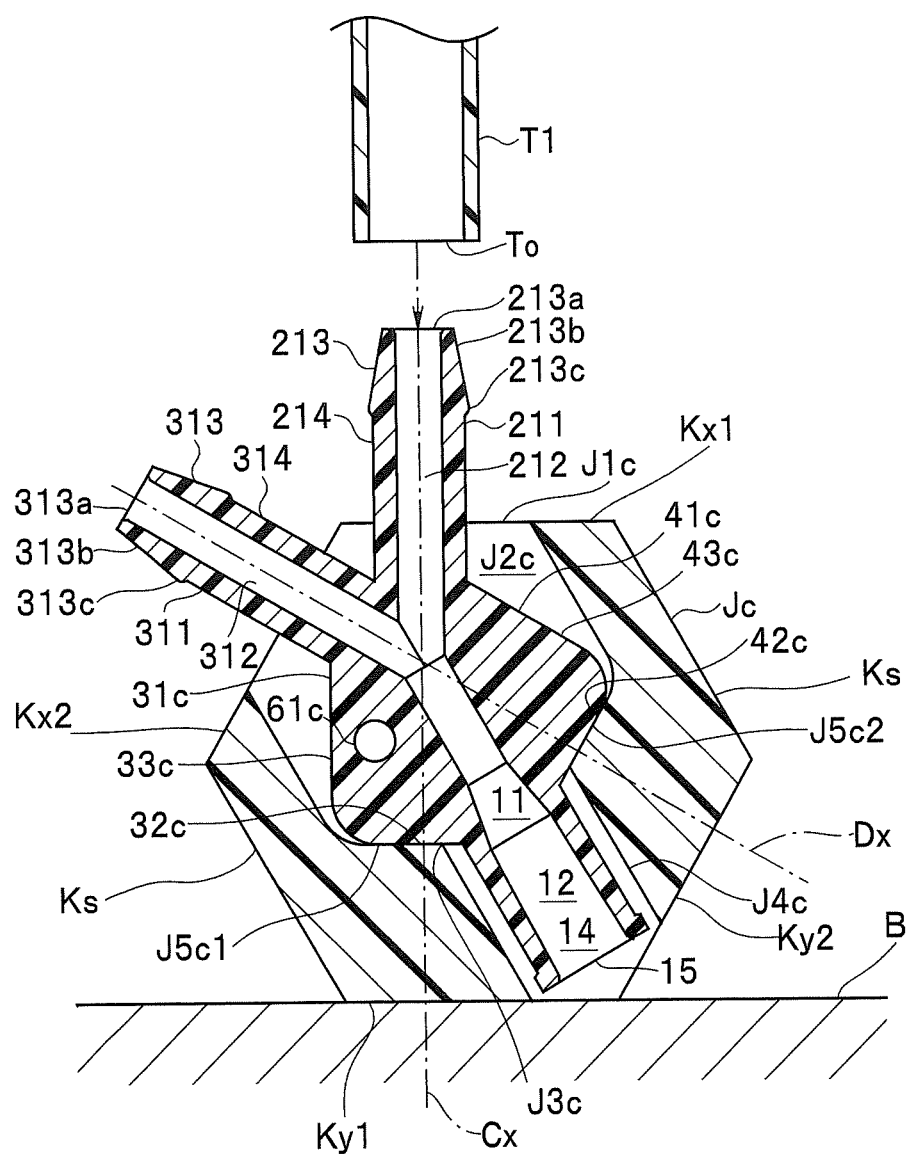
FIG. 16 is a cross-section view of the connection device and the jig according to the modification 3 of the embodiment of the present invention.
Figure 17:
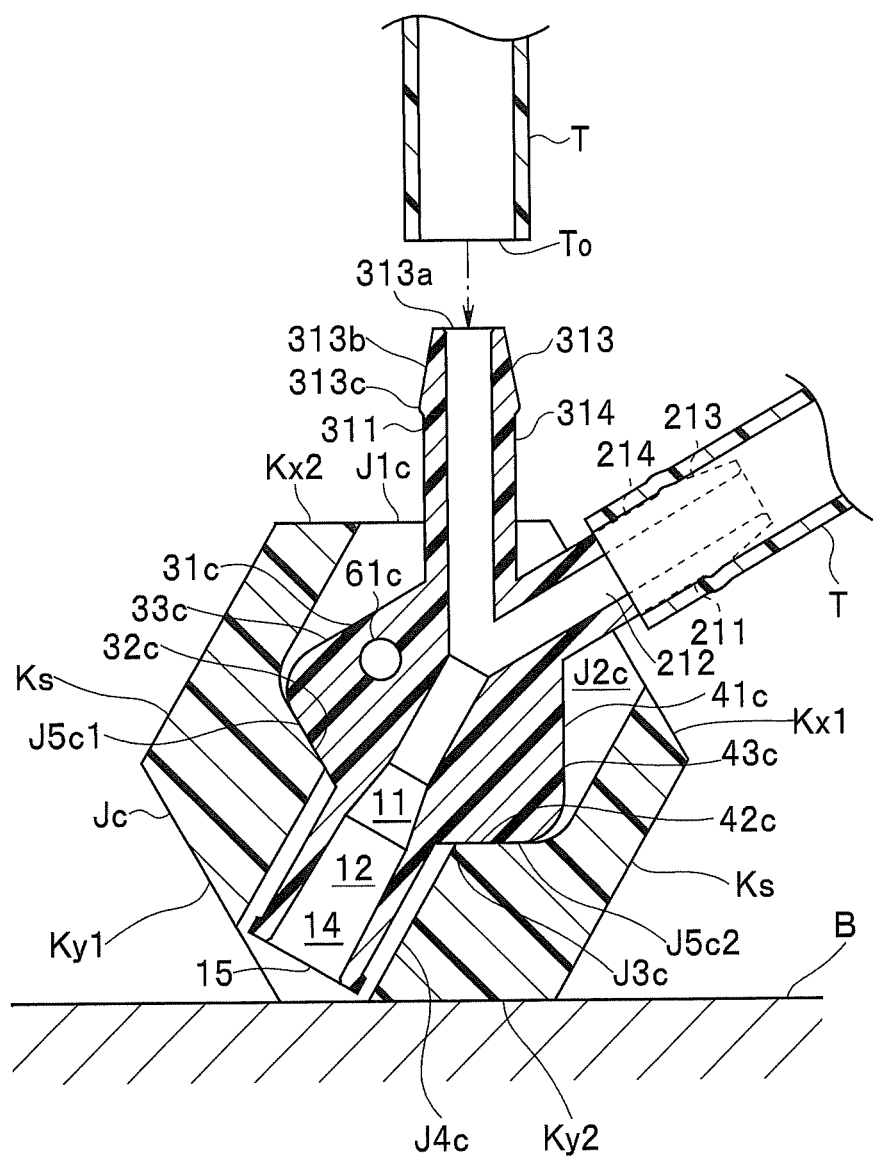
FIG. 17 is a cross-section view of the connection device and the jig according to the modification 3 of the embodiment of the present invention.

FIGS. 15, 16, and 17 are perspective views of a connection device 1c and a jig Jc according to a modification 3 of the embodiment of the present invention. In the modification, regarding configurations similar to the configurations of the other embodiment and modifications, descriptions are omitted.

As shown in FIG. 15, the connection device 1c has a branch portion 11b, a branch tube 211 that is a first branch tube, a branch tube 311 that is a second branch tube, and protruding plates 31c and 41c.

The branch portion 11b is provided in the other end portion of the tube 11.

In the branch portion 11b, branch tubes 211 and 311 are branched in a Y shape from the tube 11. Each of the branch tubes 211 and 311 is formed in a cylindrical shape and flow paths 212 and 312 for flowing a fluid are provided inside.

In other words, the tube 11 is branched to two passages on the one end portion side.

The branch tube 211 has a tube connection portion 213 and a body portion 214. The branch tube 211 extends in an opposite direction to an other end edge 32c from the branch portion 11b along a direction orthogonal to the other end edge 32c.

The tube connection portion 213 has a branch end opening 213a that is provided on a branch end and communicates with a flow path 212, a taper portion 213b that has a diameter enlarging from an outer edge of the branch end opening 213a in a direction of the branch portion 11b, and an enlarged diameter portion 213c that is provided on the side of the branch portion 11b of the taper portion 213b and has the enlarged diameter portion outer diameter Pe.

The body portion 214 has the body portion outer diameter Pb and extends from a branch portion 11b so as to be adjacent to a protruding plate 41c and intersect a side edge 43c.

The branch tube 311 has a tube connection portion 313 and a body portion 314. The branch tube 311 extends in an opposite direction to an other end edge 42c from the branch portion 11b along a direction orthogonal to the other end edge 42c. The tube connection portion 313 has a branch end opening 313a that communicates with a flow path 312, a taper portion 313b, and an enlarged diameter portion 313c.

The protruding plate 31c has the other end edge 32c, a side edge 33c, and a through-hole 61c.

On the other end side of the protruding plate 31c, the other end edge 32c protrudes from the tube 11 and extends in the direction inclined in such a manner that a distance from the tube 11 is lengthened toward one end. Note that, as shown in FIG. 16, the other end side edge 32c is provided on both sides across an axis line Cx so as to be orthogonal to the axis line Cx of the branch tube 211.

The side edge 33c extends in a direction inclined in such a manner that a distance from the tube 11 is shortened toward one end from the end portion of the other end edge 32c on the side portion side of the protruding plate 31c, and intersects the tube 11.

The through-hole 61c is formed so as to pass through front and rear faces of the protruding plate 31c.

The protruding plate 41c has the other end edge 42c and the side edge 43c.

The other end edge 42c protrudes from the tube 11 and extends in a direction inclined in such a manner that a distance from the tube 11 is lengthened toward one end on the opposite side to the other end edge 32c across the tube 11 and on the other end side of the protruding plate 41c. Note that, as shown in FIG. 16, the other end side edge 42c is provided on both sides across an axis line Dx so as to be orthogonal to the axis line Dx of the branch tube 311.

On a side portion side of the protruding plate 41c, the side edge 43c extends in a direction inclined in such a manner that a distance from the tube 11 is shortened toward one end from an end portion of the other end edge 42c, and intersects the tube 11.

The jig Jc is formed in a substantially hexagonal column shape and has one end walls Kx1 and Kx2, two side walls Ks, and the other end walls Ky1 and Ky2 that surround six passages. The one end wall Kx1 and the other end wall Ky1, and the one end wall Kx2 and the other end wall Ky2 are formed parallel to each other.

The jig Jc has an opening J1c, a protruding portion housing portion J2c, an opening for tube J3c, a tube housing portion J4c, and stopper portions J5c1 and J5c2.

The opening J1c is provided in the one end walls Kx1 and Kx2. A size of the opening J1c is adjusted and set so that the inserted connection device 1 does not fall down within the jig Jc.

The protruding portion housing portion J2c is concaved from the opening J1c. A circumferential wall of the protruding portion housing portion J2c extends from the opening J1c. A length in a depth direction of the protruding portion housing portion J2c is set to a length such that the tube connection portions 213 and 313 protrude from the one end walls Kx1 and Kx2.

The opening for tube J3c is provided in the center of a bottom portion of the protruding portion housing portion J2c. The opening for tube J3c has an inner diameter larger than an outer diameter of the tube 11 so as to insert the tube 11.

The tube housing portion J4c is formed so as to pass through the other end walls Ky1 and Ky2 from the opening for tube J3c.

The stopper portions J5c1 and J5c2 are provided on both sides across the opening for tube J3c in the bottom portion of the protruding portion housing portion J2c. The stopper portion J5c1 is provided so as to be parallel to the other end wall Ky1. The stopper portion J5c2 is provided so as to be parallel to the other end wall Ky2.

When the connection device 1c is inserted into the jig Jc, the other end portion of the tube 11 is internally inserted into the tube housing portion J4c through the opening J1c, the protruding portion housing portion J2c, and the opening for tube J3c. When the connection device 1c is inserted shifting from the opening for tube J3c, the other end portion of the tube 11 is contacted with the stopper portions J5c1 and J5c2 and is guided to an insertion opening.

As shown in FIG. 16, the user directs the other end wall Ky1 downward and places the connection device 1c on the mounting place B so that the tube connection portion 13 is directed upward.

The user grasps the flexible tube T and externally fits and pushes the end portion opening To of the flexible tube T in an outer edge of the branch end opening 213a of the tube connection portion 213. The other end edge 32c is stopped by the stopper portion J5c1 and the flexible tube T is connected to the tube connection portion 213.

As shown in FIG. 17, the user directs the other end wall Jy2 downward and places the jig Jc on the mounting place B so that the tube connection portion 313 is directed upward.

The user grasps the flexible tube T and externally fits and pushes the end portion opening To of the flexible tube T in an outer edge of the branch end opening 313a of the tube connection portion 313. The other end edge 42c is stopped by the stopper portion J5c2 and the flexible tube T is connected to the tube connection portion 313.

Thereby, the connection device 1c is attached to the jig Jc, and in a stable state, the flexible tube T can be connected to each of the tube connection portions 213 and 313 and the work efficiency of the connection work can be caused to be improved.

(Modification 4 of Embodiment)

Figure 18:
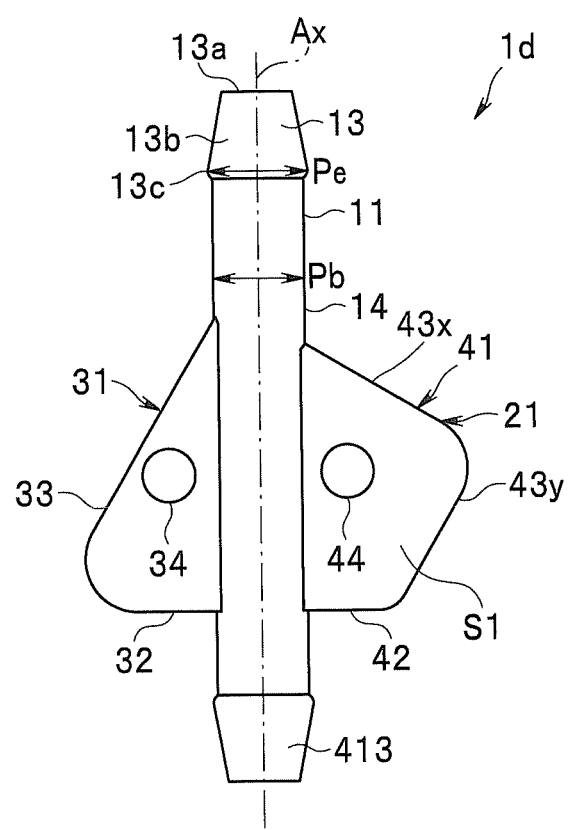
FIG. 18 is a front view of the connection device according to a modification 4 of the embodiment of the present invention.

FIG. 18 is a front view of a connection device 1d according to a modification 4 of the embodiment of the present invention.

In the embodiment and the modifications, the luer lock 15 is provided on the other end portion of the tube 11 and a syringe is connected to the luer lock 15. However, it does not matter if the luer lock 15 is not provided. In this case, as shown in FIG. 18, for example, it does not matter if a tube connection portion 413 is provided on the other end portion of the tube 11 of the connection device 1d and the other flexible tube is connected to the tube connection portion 413. A configuration of the tube connection portion 413 is similar to the configuration of the tube connection portion 13, and therefore descriptions are omitted.

The connection device 1d can also be attached to the jig J. The other flexible tube is connected to the other end portion of the tube 11.

Thereby, the connection device 1d can connect the flexible tube T and the other flexible tube.

Note that, in the embodiment and the modifications, the user grasps the flexible tube T and connects the flexible tube T to the connection device 1c by fingers. However, it does not matter if the user grasps the flexible tube T and connects the flexible tube T to the connection device 1c by a device.

The present invention is not intended to be limited to the embodiment described above, and within the range not changing the gist of the present invention, various changes and modifications are possible.

According to the present invention, a connection device that is attached to a jig, and in a stable state, to which a flexible tube can be connected and in which a work efficiency of connection work can be caused to be improved can be provided.

What is claimed is:

1. A connection device comprising:
    a tube branched to first and second passages from a branch portion, the first and second passages including a first branch tube and a second branch tube, respectively, that are provided on an end side of the tube;
    a first protruding plate provided so as to protrude from an outer circumference portion of the tube, the first protruding plate including a first end edge extending in a direction orthogonal to a first longitudinal axis line of the first branch tube, the first end edge being a portion of an outer periphery of the first protruding plate; and
    a second protruding plate provided so as to face the first protruding plate across the tube and protrude in a diameter direction of the tube, the second protruding plate including, a second end edge extending so as to be orthogonal to a second longitudinal axis line of the second branch tube;
    wherein the first and second end edges are configured to be abutted to corresponding surfaces of a jig when a flexible tube is connected to one or more of the first branch tube and the second branch tube.

2. The connection device according to claim 1, wherein at least one of the first branch tube and the second branch tube having:
    a body portion; and
    an enlarged diameter portion provided at one end;
    wherein a first outer diameter of the body portion is equal to or smaller than an inner diameter of the flexible tube and a second outer diameter of the enlarged diameter portion is larger than the tube inner diameter.

3. The connection device according to claim 1, further comprising a luer lock configured to connect to a syringe, the luer lock being arranged at an other end side of the tube.

4. The connection device according to claim 1, wherein an other end side of the tube is configured to be connected to a flexible tube.

5. A connection device comprising:
    a tube branched to first and second passages from a branch portion, the first and second passages including a first branch tube and a second branch tube, respectively, that are provided on an end side of the tube;
    a first protruding plate provided so as to protrude from an outer circumference portion of the tube, the first protruding plate including a first end edge extending in a direction orthogonal to a first longitudinal axis line of the first branch tube, the first end edge being a portion of an outer periphery of the first protruding plate; and
    a second protruding plate provided so as to face the first protruding plate across the tube and protrude in a diameter direction of the tube, the second protruding plate including, a second end edge extending so as to be orthogonal to a second longitudinal axis line of the second branch tube;
    wherein:
    the first protruding plate further comprises a first side edge that extends to the first end edge and extends in a direction inclined relative to the first end edge such that a first distance from the first branch tube to the first side edge is shortened toward the end side; and
    the second protruding plate further comprises a second side edge that extends to the second end edge and extends in a direction inclined relative to the second end edge such that a second distance from the second branch tube is shortened toward the end side.

6. The connection device according to claim 1, wherein the first end edge is arranged on both sides across the first longitudinal axis line of the first branch tube.

7. A connection device comprising:
a tube branched to first and second passages from a branch portion, the first and second passages including a first branch tube and a second branch tube, respectively, that are provided on an end side of the tube;
a first protruding plate provided so as to protrude from an outer circumference portion of the tube, the first protruding plate including a first end edge extending in a direction orthogonal to a first longitudinal axis line of the first branch tube, the first end edge being a portion of an outer periphery of the first protruding plate; and
a second protruding plate provided so as to face the first protruding plate across the tube and protrude in a diameter direction of the tube, the second protruding plate including, a second end edge extending so as to be orthogonal to a second longitudinal axis line of the second branch tube;
wherein the second end edge is arranged on both sides across the second longitudinal axis line of the second branch tube.

8. A connection device set, comprising:
a connection device comprising;
a tube branched to first and second passages from a branch portion, the first and second passages including a first branch tube and a second branch tube, respectively, that are provided on an end side of the tube;
a first protruding plate provided so as to protrude from an outer circumference portion of the tube, the first protruding plate including a first end edge extending in a direction orthogonal to a first longitudinal axis line of the first branch tube, the first end edge being a portion of an outer periphery of the first protruding plate; and
a second protruding plate provided so as to face the first protruding plate across the tube and protrude in a diameter direction of the tube, the second protruding plate including, a second end edge extending so as to be orthogonal to a second longitudinal axis line of the second branch tube; and
a jig having surfaces abutted to the first and second end edges when a flexible tube is connected to the first and second branch tubes.

9. The connection device according to claim 1, wherein the second end edge is an outer periphery of the second protruding plate.

* * * * *